(12) United States Patent
Pluntke et al.

(10) Patent No.: US 9,478,613 B2
(45) Date of Patent: Oct. 25, 2016

(54) SEMICONDUCTOR SYSTEM FOR A CURRENT SENSOR IN A POWER SEMICONDUCTOR

(71) Applicant: Robert Bosch GmbH, Stuttgart (DE)

(72) Inventors: Christian Pluntke, Hechingen (DE); Timm Hoehr, Ruetlingen (DE); Thomas Jacke, Tuebingen (DE); Frank Wolter, Munich (DE); Holger Ruething, Munich (DE); Guenther Koffler, Ledenitzen (AT)

(73) Assignee: Robert Bosch GmbH, Stuttgart (DE)

( * ) Notice: Subject to any disclaimer, the term of this patent is extended or adjusted under 35 U.S.C. 154(b) by 25 days.

(21) Appl. No.: 14/378,718

(22) PCT Filed: Jan. 25, 2013

(86) PCT No.: PCT/EP2013/051415
§ 371 (c)(1),
(2) Date: Aug. 14, 2014

(87) PCT Pub. No.: WO2013/120680
PCT Pub. Date: Aug. 22, 2013

(65) Prior Publication Data
US 2014/0374795 A1 Dec. 25, 2014

(30) Foreign Application Priority Data
Feb. 14, 2012 (DE) .......................... 10 2012 202 180

(51) Int. Cl.
*H01L 29/06* (2006.01)
*H01L 29/739* (2006.01)
*G01N 29/44* (2006.01)
(Continued)

(52) U.S. Cl.
CPC ............ *H01L 29/0696* (2013.01); *G01H 5/00* (2013.01); *G01N 29/07* (2013.01); *G01N 29/4463* (2013.01); *G01N 29/46* (2013.01);
(Continued)

(58) Field of Classification Search
None
See application file for complete search history.

(56) References Cited

U.S. PATENT DOCUMENTS

| | | | |
|---|---|---|---|
| 6,180,966 B1 * | 1/2001 | Kohno et al. | 257/173 |
| 2005/0286194 A1 | 12/2005 | Fujiki et al. | |

(Continued)

FOREIGN PATENT DOCUMENTS

| | | |
|---|---|---|
| DE | 10 2006 0489 | 4/2008 |
| FR | 2 943 341 | 2/2004 |
| JP | 11-17179 A | 1/1999 |
| JP | 2005-322781 A | 11/2005 |
| JP | 2007 287988 | 11/2007 |
| JP | 2010-238993 A | 10/2010 |
| WO | WO 2011/161721 | 12/2011 |

OTHER PUBLICATIONS

International Search Report for PCT/EP2013/051415, dated May 14, 2013.

*Primary Examiner* — Erik Kielin
(74) *Attorney, Agent, or Firm* — Maginot, Moore & Beck LLP

(57) ABSTRACT

A semiconductor system for a current sensor in a power semiconductor includes: on a substrate, a multiple arrangement of transistor cells having an insulated gate electrode, whose emitter terminals are connected in a first region via a first conductive layer to at least one output terminal and whose emitter terminals are connected in a second region via a second conductive layer to at least one sensor terminal, which is situated outside of a first cell region boundary, which encloses the transistor cells of the first region and the second region, a trench structure belonging to the first cell region boundary being developed between the transistor cells of the second region and the sensor terminal.

8 Claims, 7 Drawing Sheets

(51) Int. Cl.
*G01N 29/46* (2006.01)
*G01N 29/07* (2006.01)
*G01S 7/53* (2006.01)
*G01S 15/10* (2006.01)
*G01H 5/00* (2006.01)

(52) U.S. Cl.
CPC ................ *G01S 7/53* (2013.01); *G01S 15/10* (2013.01); *H01L 29/7393* (2013.01)

(56) References Cited

U.S. PATENT DOCUMENTS

2008/0230810 A1    9/2008   Yoshimura
2010/0320461 A1   12/2010   Su et al.
2013/0168700 A1*   7/2013   Furukawa et al. .............. 257/77

* cited by examiner

SEMICONDUCTOR SYSTEM FOR A CURRENT SENSOR IN A POWER SEMICONDUCTOR

BACKGROUND OF THE INVENTION

1. Field of the Invention

The present invention relates to a semiconductor system for a current sensor in a power semiconductor, e.g., for a power semiconductor of the type of a bipolar transistor having an insulated gate electrode, which is also called an insulated gate bipolar transistor (IGBT).

2. Description of the Related Art

Power semiconductors are usually manufactured as a vertical structure and have a plurality of transistor cells. In the process, gate and emitter structures are formed on the front side of a semiconductor substrate, which are connected via at least one p-n junction to the collector layer developed on the back side as a metallic coating over the entire surface. In power transistors, this cell structure is repeated over a large region of the substrate such that high currents may be transmitted. In so doing, care must be taken, however, to avoid short circuit states or overload states. Thus it is known from the general related art to attach a shunt resistor on the output terminal in order to detect possibly occurring short circuits or overload states in the primary current circuit.

The related art also teaches to branch off a region of the emitter or a portion of the emitter cells via a sensor terminal and to utilize the current flowing there as a signal. The sensor terminal is typically located within the emitter region and is entirely or partially filled with emitter cells. In the case of complete filling, the embedding of the sensor cells in the main emitter is very tight and it is to be expected that the behavior of the sensor cells deviates only slightly from that of the main emitter cells. Because of the relative sizes of the emitter terminal and the sensor terminal, however, a fixed ratio of sensor current to primary current is predefined. The case of a merely partial filling offers the advantage of being able to design this ratio more freely, but the tight embedding is lost and there are cell-free regions in which a charge carrier plasma likewise builds up in the conductive state.

When using or even already when designing an IGBT, care must be taken so that the charge carriers running off through the emitter in the switch-off case do not overload the individual transistor cells. In the example of an IGBT having an n channel, the charge carrier species running off through the emitter is provided by holes. The danger of overloading and the triggering of a latch-up exists specifically for the cells located on the edges of the sensing region and the main emitter region since a charge carrier plasma forms also in the cell-free regions without emitter contacts. This intermediate region that contains no cells (cell-free region) exists on the one hand when the sensor terminal is incompletely filled, although it also results from the necessity of having to separate the conductive layers connected to the two emitter regions.

BRIEF SUMMARY OF THE INVENTION

The objective of the present invention is to reduce the load on the cells bordering cell-free regions through the holes of the load carrier plasma located in the cell-free regions running off in the case of a switch-off and at the same time to allow for the tightest possible embedding of the sensor cells in the main emitter.

This objective is achieved by a circuit configuration for a power semiconductor, which comprises a multiple arrangement of transistor cells having an insulated gate electrode on a substrate, the emitter terminals of which are connected in a first region via a first conductive layer to at least one output terminal and whose emitter terminals are connected in a second region via a second conductive layer to at least one sensor terminal. The sensor terminal is situated outside of a first cell boundary, which encloses the transistor cells of the first region and the transistor cells of the second region. A trench structure belonging to the first cell region boundary is developed between the transistor cells of the second region and the sensor terminal, which is followed in the direction toward and outer edge of the substrate by a doped layer connected to the first conductive layer and which furthermore continues between the transistor cells of the first region and the transistor cells of the second region.

According to the present invention, the emitter made up of the IGBT cells is divided into two cell groups. On the one hand, main cells are formed, which are connected to the emitter output via the first conductive layer. This cell group occupies the largest part of the substrate area of the circuit configuration. The smaller part connected to the second conductive layer is provided as sensor cells and is used as a current sensor such that a voltage signal is able to be generated via an external resistor, which is able to be processed further for detecting short circuit currents and overcurrents. The doped region adjoining the first conductive layer is used to discharge the holes running off in the switch-off process such that these no longer place a load on the adjacent main cells, which could result in a heightened danger of latch events and thus to the destruction of the chip.

The objective of the present invention is achieved by the fact that the terminal of the sensor is placed outside of the active cell region behind the cell region boundary. The holes stemming from this terminal region are discharged via the doped region connected via the conductive layer of the main emitter. Moreover, the size and shape of the sensor region may thus be designed independently of the size and shape of the sensor terminal.

According to another development of the present invention, the transistor cells of the second region are arranged in the shape of an arbitrary polygon, preferably in the shape of a semicircle, or a polygon approximating a semicircle, or a rectangle or a square.

These arrangements may be formed readily as a repeating structure using the usual layout programs and are able to be implemented using the common manufacturing processes for power semiconductors.

According to another development of the present invention, the transistor cells of the first region enclose the transistor cells of the second region at least partially, preferably on three sides.

According to another development of the present invention, the transistor cells of the first region enclose the transistor cells of the second region completely.

According to another development of the present invention, the transistor cells of the second region are spatially separated from the transistor cells of the first region.

In this specific embodiment, the current sensor cells are not embedded tightly into the main cells, but are rather surrounded by their own cell region boundary far away from the main cells. This corresponds to a separated smaller IGBT semiconductor, the plasma of which in the switched-on state or during the switching processes interacts very little to not at all with the plasma of the main IGBT depending on the distance. Nevertheless, both parts are still to be regarded as one IGBT chip since they are surrounded by a common edge termination structure in the direction toward the edge of the chip.

According to another development of the present invention, the sensor terminal is situated as a metallic coating above an insulation layer, the layer thickness of which is greater than the one of a gate dielectric.

In this specific embodiment, the sensor terminal is able to be placed in any location above a thick oxide.

According to another development of the present invention, the transistor cells of the second region are surrounded by a second cell region boundary.

This specific embodiment is used especially when the sensor cells are arranged at a far removed location from the main cells.

According to another development of the present invention, the sensor terminal and the transistor cells of the second region are situated outside of the cell region boundary.

In this specific embodiment, there is no dual-trench structure between the sensor terminal and the transistor cells of the second region.

The second conductive layer may have a notch in the region of the cell region boundary, in which the first conductive layer is connected to the doped layer. This results in another improvement of the discharge of the holes running off in the switch-off process.

The present invention is explained in greater detail below on the basis of exemplary embodiments with reference to the enclosed drawing.

BRIEF DESCRIPTION OF THE DRAWINGS

FIG. 3 shows another schematic representation of the specific embodiment according to FIG. 2a.

DETAILED DESCRIPTION OF THE INVENTION

Figure 1:
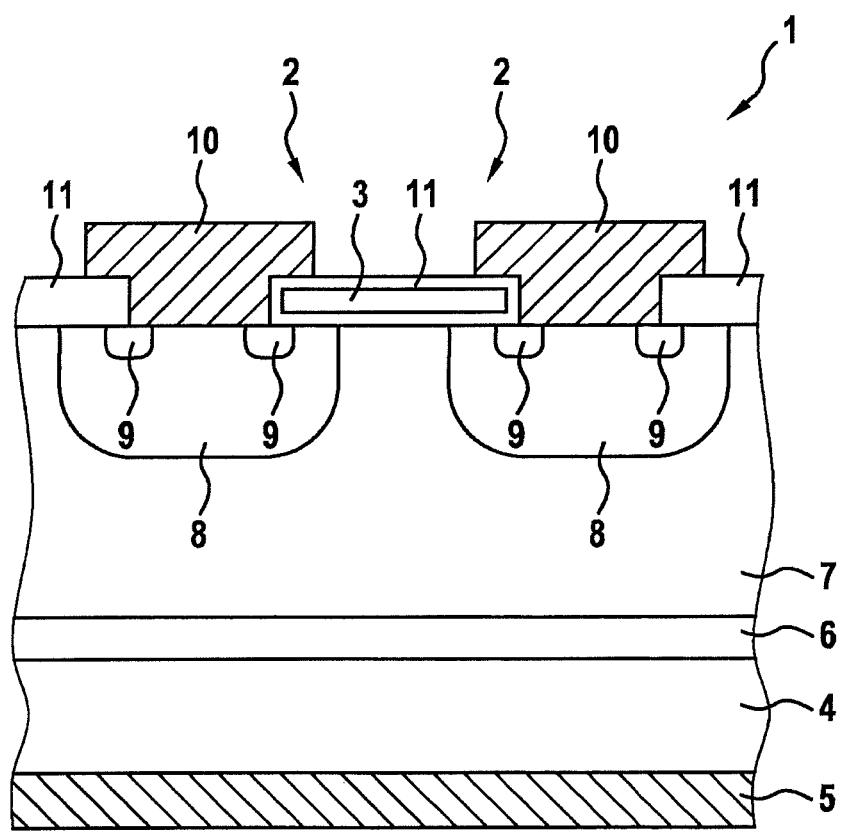
FIG. 1 shows transistor cells in a cross-sectional view.

Identical elements, or elements acting in identical manner, have been provided with the same reference numerals in the figures.

FIG. 1 shows a section of a circuit configuration 1, which represents a base cell for a plurality of transistor cells 2 having an insulated gate electrode 3 (IGBT). As shown in FIG. 1, a substrate 4, which is p+-doped for example, includes on a back side a collector terminal 5, which is normally applied as a metal layer. A buffer layer 6, which is n-doped in this example, is applied above collector terminal 5 and substrate 4 and is followed by a likewise n-doped epitaxy layer 7. In epitaxy layer 7, p-doped troughs 8 are situated, by ion implantation for example, in which respectively two n-doped islands 9 are situated, which together with p-doped trough 8 are partially covered by an emitter terminal 10.

Gate electrode 3 is surrounded by an insulating layer 11 formed from silicon oxide, which may also be situated outside of transistor cell 2. Altogether, an n+pnp+-structure is obtained for an n-channel IGBT in the example shown. It is also conceivable, however, to apply the present invention in the case of other IGBT types, for example a p-channel IGBT or an IGBT having a vertical structure.

Figure 2A:
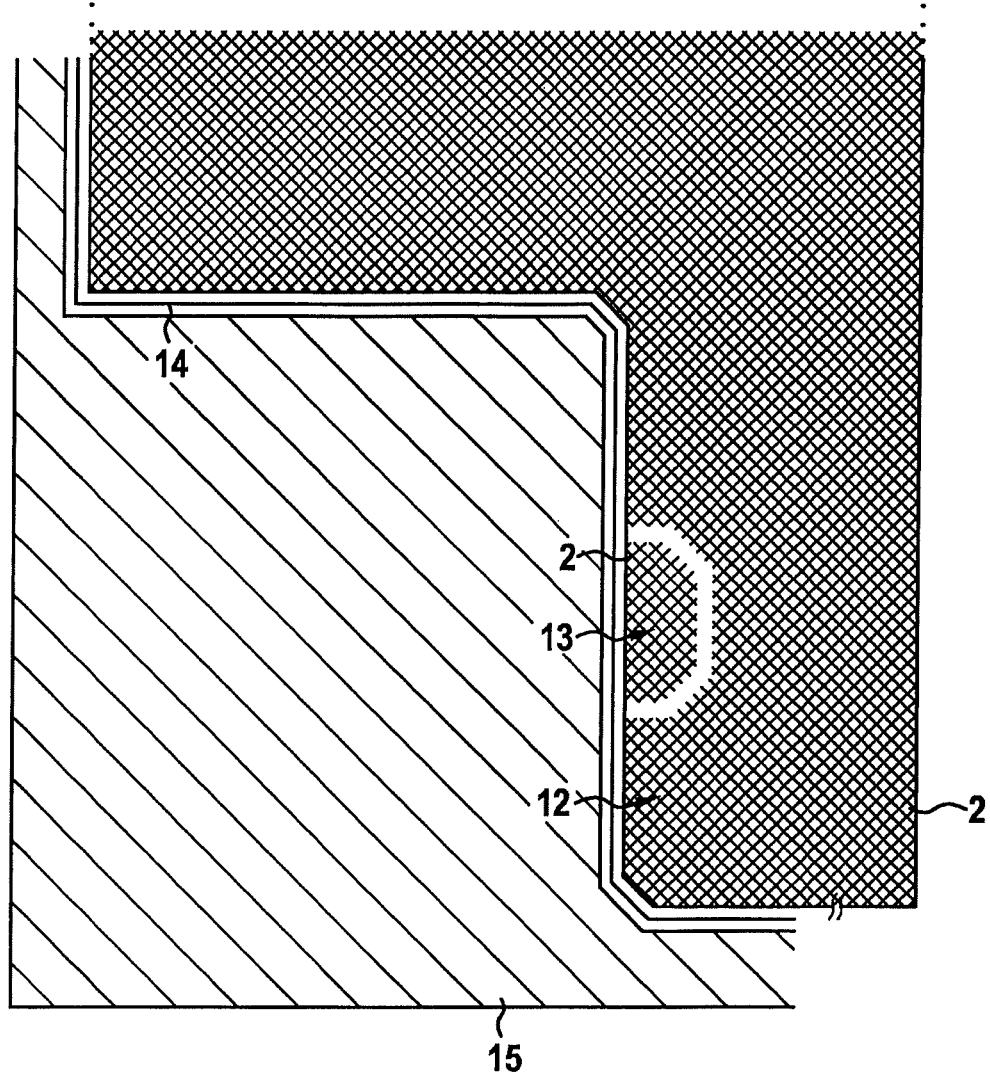
FIG. 2a shows a semiconductor system of the present invention in a top view according to a first specific embodiment of the invention.

Circuit configuration 1 is described in the following according to a first specific embodiment of the present invention. FIG. 2a shows circuit configuration 1 in a top view, i.e. onto the topside having emitter terminals 10. As may be seen from FIG. 2a, circuit configuration 1 includes a plurality of transistor cells 2, which are situated in a first region 12 and in a second region 13. The system shown in FIG. 2a is to be understood merely by way of example.

Transistor cells 2 cover first region 12 and second region 13 essentially completely and may be arranged in any desired pattern, which does not necessarily need to be regular. Transistor cells 2 of first region 12 are connected in parallel and are used for the power semiconductor.

Transistor cells 2 of second region 13 are likewise connected in parallel and are used for a current sensor, as will be explained in more detail below. Transistor cells 2 of first region 12 may be called main cells, while those of the second region 13 are called sensor cells.

The transistor cells 2 of first region 12 and the transistor cells 2 of second regions 13 are surrounded by a first cell region boundary, the cell region boundary being indicated by reference numeral 14. First cell region boundary 14 is developed in the substrate in the form of a trench. It is also possible, however, to use a dual-trench structure, which is formed by two trenches running side-by-side in the substrate. The region outside of first cell region boundary 14 is provided with a doped layer 15, which is a p-doped layer in the exemplary embodiment shown. Doped layer 15 is drawn in FIG. 2a as a shaded area.

Figure 2B:
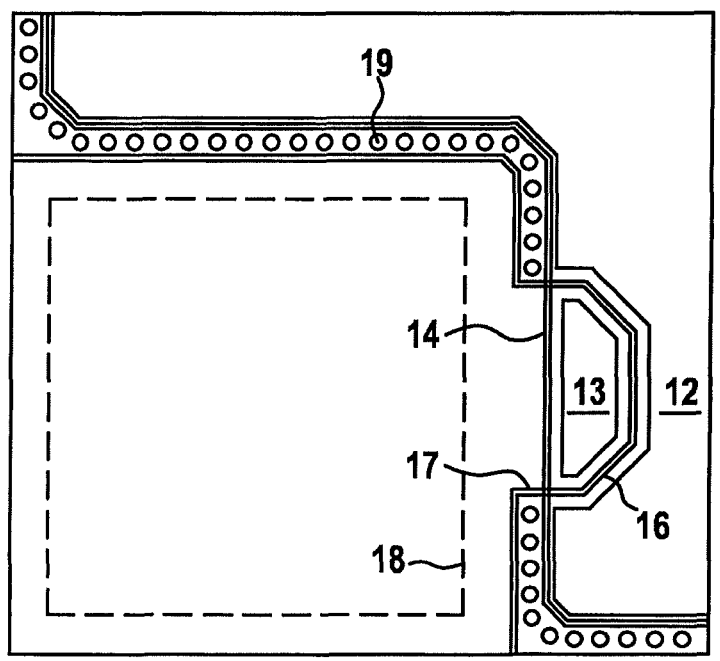
FIG. 2b shows a semiconductor system of the present invention in another top view according to the first specific embodiment of the invention.

With reference to FIG. 2b, the contacting of transistor cells 2 of first region 12 and of transistor cells 2 of second region 13 will be explained in more detail in the following. The contacting occurs via metallic coating layers that connect emitter terminals 10 as shown in FIG. 1. For better representation, transistor cells 2 of first region 12 and transistor cells 2 of second region 13 as well as p-doped layer 15 are not drawn in FIG. 2b.

The emitter terminals of transistor cells 2 of first region 12 are connected via a first conductive layer 16. Via suitable output terminals, first conductive layer 16 may be used as the output of the power transistor, in which the outputs of transistor cells 2 of first region 12 are provided.

Emitter terminals 10 of transistor cells 2 of second region 13 are connected via a second conductive layer 17 to at least one sensor terminal. The sensor terminal may be connected to an external resistor via a bonding wire, as will be explained further below. Second conductive layer 17 also functions as a sensor terminal. The sensor terminal is schematically indicated by reference numeral 18 in FIG. 2b. In this manner, an electrical connection is established between the emitter terminals of transistor cells 2 of second region 13 and sensor terminal 18.

As shown in FIG. 2b, a gap exists between first conductive layer 16 and second conductive layer 17 such that the emitter terminals of these regions are not connected to one another.

As already explained in connection with FIG. 2a, below sensor terminal 18 there is the p-doped layer 15, which is situated on an outer edge of first edge structure 14. This region is connected to first conductive layer 16 via contacts 19. Consequently, p-doped layer 15 is able to allow for the discharge of the holes discharging in the switch-off process such that these do not place a load on the neighboring cells of transistor cells 2 of first region 12.

Figure 3:
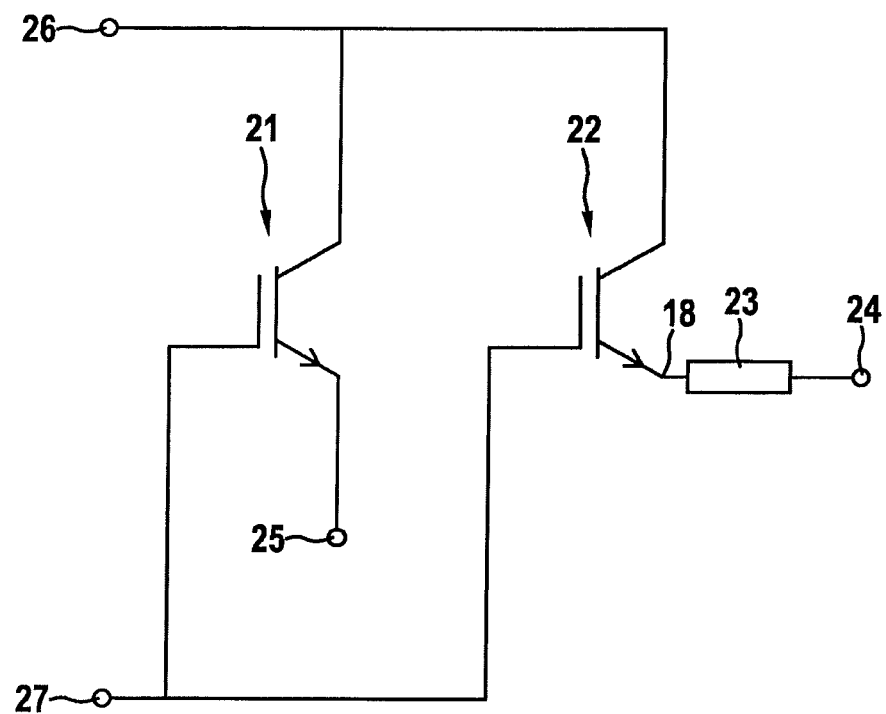

Circuit configuration 1 as it is shown in FIG. 1, FIG. 2a and FIG. 2b is summarized once more schematically in FIG. 3. Transistor cells 2 of first region 12 form main cell IGBT 21. Transistor cells 2 of second region 13 form sensor cell IGBT 22. The respective collector terminals of the two IGBTs may be connected to a terminal 26, and those of the gate terminals may be connected to the additional terminal 27. Emitter terminal 10 of main cell IGBT 21 is connected to output terminal 25. Emitter terminal 10 of sensor cell IGBT 22 is connected via sensor terminal 18 to a component, which may be an external ohmic resistor 23 for example, it being possible to detect a short-circuit state or overload state on output terminal 25 via signal 24.

Additional specific embodiments of the present invention are described in the following. Essentially, the differences with respect to the exemplary embodiment shown in connection with FIG. 2 are explained in the process.

Figure 4:
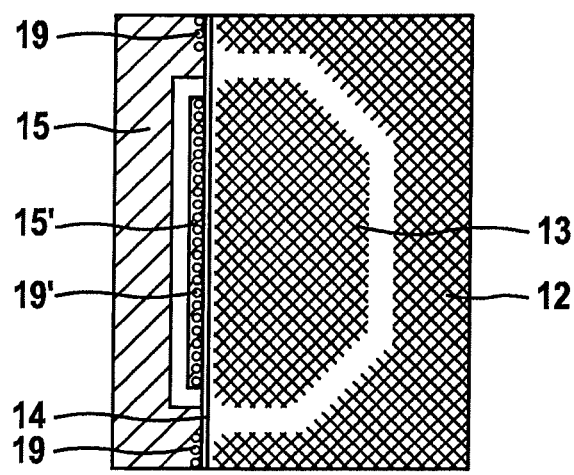
FIG. 4 shows a semiconductor system of the present invention in a top view according to another specific embodiment of the invention.

In FIG. 4, in addition to transistor cells 2 of second region 13, another p-doped region 15' is situated in the direction of sensor terminal 18, which is separated from p-doped region 15. The additional p-doped region 15' is connected to second conductive layer 17 (not shown in FIG. 4) via additional contacts 19'.

Figure 5:
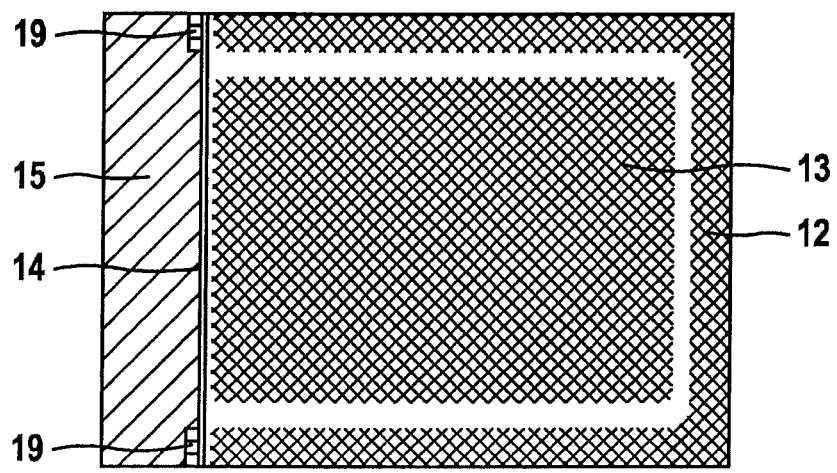
FIG. 5 shows a semiconductor system of the present invention in a top view according to another specific embodiment of the invention.

FIG. 5 shows a variant of the arrangement of transistor cells 2 of second region 13. In this specific embodiment, transistor cells 2 of second region 13 are arranged in a rectangular shape. Moreover, it is also conceivable to provide another arrangement for the transistor cells 2 of second region 13, which is compatible with manufacturing processes. Thus it is possible for the transistor cells 2 of second region 13 to be arranged in the shape of an arbitrary polygon, preferably in the shape of a semicircle, or a polygon approximating a semicircle, or a rectangle or a square.

Figure 6:
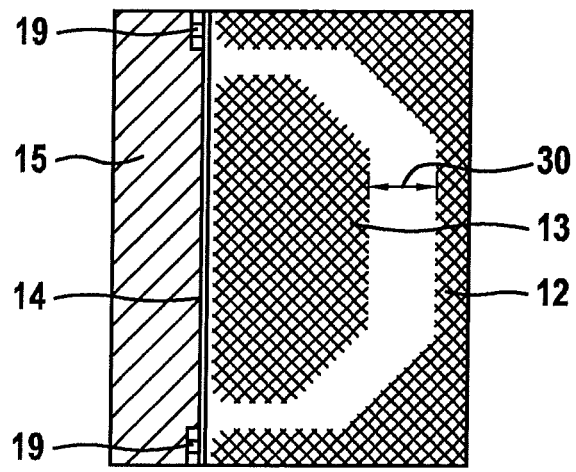
FIG. 6 shows a semiconductor system of the present invention in a top view according to another specific embodiment of the invention.

FIG. 6 shows another variant of the arrangement of the transistor cells 2 of first region 12 and of the transistor cells 2 of second region 13. In this specific embodiment, the transistor cells 2 of first region 12 and the transistor cells 2 of second region 13 are spaced at a greater distance 30 from each other. While in the previously shown specific embodiments the distance between the transistor cells 2 of first region 12 and the transistor cells 2 of second region 13 exceeds the diameter of the transistor cells 2 only slightly, distance 30 may correspond for example to the tenfold diameter of transistor cells 2 as shown in FIG. 6.

Figure 7:
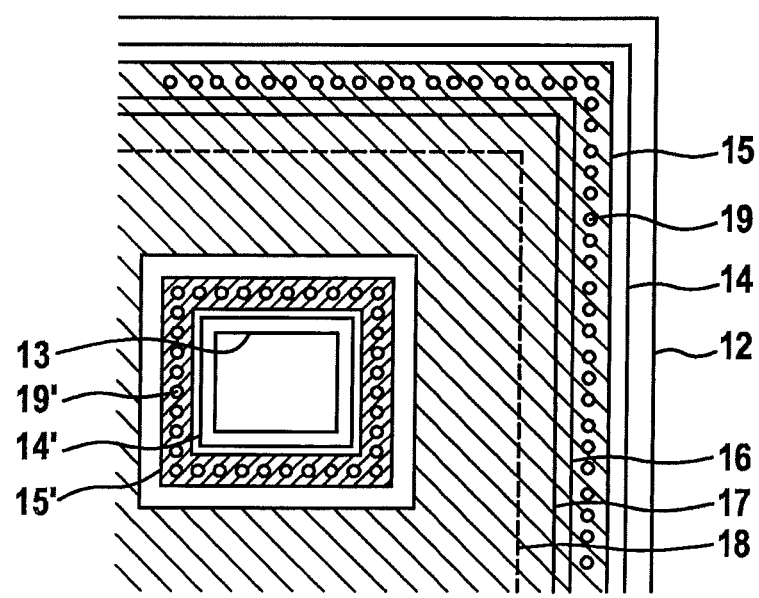
FIG. 7 shows a semiconductor system of the present invention in a top view according to another specific embodiment of the invention.

FIG. 7 shows an exemplary embodiment in which the transistor cells 2 of second region 13 are surrounded by a second cell region boundary 14', which again may be developed as a dual-trench structure. Transistor cells 2 of second region 13 are in this instance not embedded in transistor cells 2 of first region 12 or partially surrounded by the latter, but are rather situated at a far distance from transistor cells 2 of first region 12. A corresponding opening of the thick oxide situated in this region allows for a connection to sensor terminal 18.

Transistor cells 2 of second region 13 are surrounded by another p-doped layer 15'. Transistor cells 2 of first region 12 are surrounded outside of first cell region boundary 14 by p-doped layer 15. P-doped layers 15 and 15' are separated from each other. Analogously to the above-described specific embodiments, p-doped layer 15 is connected to first conductive layer 16 by contacts 19. The additional p-doped region 15' is connected to second conductive layer 17 via additional contacts 19'. Conductive layers 16 and 17 are again separated from each other. In this example, doped layers 15 and 15' are separated close to contacts 19'. This gap, however, could just as well run elsewhere between 19 and 19'. This analogously applies to the separation gap between conductive layers 16 and 17.

Figure 8:
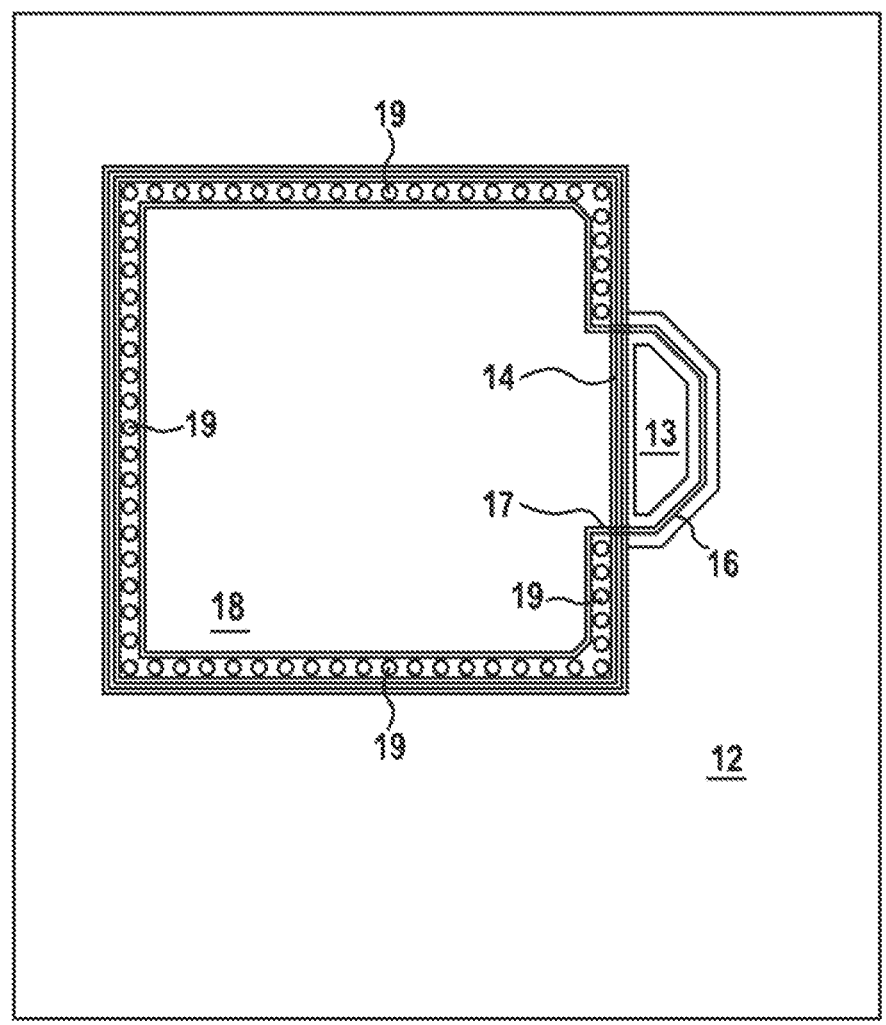
FIG. 8 shows a semiconductor system of the present invention in a top view according to another specific embodiment of the invention.

By contrast, in FIG. 8, transistor cells 2 of second region 13 are embedded together with sensor terminal 18 into the field of transistor cells 2 of first region 12. For this purpose, cell region boundary 14 is situated in such a way that it surrounds sensor terminal 18.

What is claimed is:

1. A semiconductor system for a current sensor in a power semiconductor, comprising:
    a substrate; and
    an arrangement of multiple transistor cells provided on the substrate and including an insulated gate electrode and emitter terminals, the emitter terminals being
        (i) connected in a first region via a first conductive layer to at least one output terminal and
        (ii) connected in a second region via a second conductive layer to at least one sensor terminal,
    wherein, at least one trench in the substrate encloses transistor cells of the first region and transistor cells of the second region, and
    wherein the at least one trench is provided between the transistor cells of the second region and a portion of the at least one sensor terminal when the portion of the at least one sensor terminal is projected onto the substrate, and
    wherein the at least one trench is followed in the direction of an outer edge of the substrate by a doped layer connected to the first conductive layer.

2. The semiconductor system as recited in claim 1, wherein the at least one trench comprises is a dual-trench structure.

3. The semiconductor system as recited in claim 1, wherein the transistor cells of the second region are arranged in the shape of one of a semicircle, a hexagon, a rectangle or a square.

4. The semiconductor system as recited in claim 3, wherein the transistor cells of the first region enclose the transistor cells of the second region on three sides.

5. The semiconductor system as recited in claim 3, wherein the transistor cells of the first region enclose the transistor cells of the second region and the second conductive layer completely.

6. The semiconductor system as recited in claim 3, wherein the transistor cells of the second region are spatially separated from the transistor cells of the first region.

7. The semiconductor system as recited in claim 6, wherein the at least one sensor terminal is situated as a metallic coating layer above an insulating layer having a layer thickness which is greater than a layer thickness of a gate dielectric.

8. The semiconductor system as recited in claim 6, wherein the transistor cells of the second region are surrounded by a cell region boundary.

\* \* \* \* \*